United States Patent

Takada

[11] Patent Number: 5,516,787
[45] Date of Patent: May 14, 1996

[54] INSECTICIDAL/ACARICIDAL COMPOSITION

[75] Inventor: Yoji Takada, Toyonaka, Japan

[73] Assignee: Sumitomo Chemical Company, Limited, Osaka, Japan

[21] Appl. No.: 358,941

[22] Filed: Dec. 19, 1994

[30] Foreign Application Priority Data

Dec. 20, 1993 [JP] Japan .................................. 5-319599

[51] Int. Cl.⁶ .............................. A01N 37/34; A01N 43/56
[52] U.S. Cl. .............................................. 514/407; 514/521
[58] Field of Search ....................................... 514/407, 521

[56] References Cited

U.S. PATENT DOCUMENTS 5,232,940  8/1993  Hatton et al. ............................ 514/407

FOREIGN PATENT DOCUMENTS 0295117  6/1988  European Pat. Off. .
0295118  12/1988  European Pat. Off. .
0435609  12/1990  European Pat. Off. .
0445931  9/1991  European Pat. Off. .
WO8703781  7/1987  WIPO .

OTHER PUBLICATIONS

Chem. Abstracts 118:228183 1992.
Worthing et al., The Pesticide Manual, 9th Ed. (1991 p. 214.

*Primary Examiner*—Allen J. Robinson
*Attorney, Agent, or Firm*—Birch, Stewart, Kolasch & Birch

[57] ABSTRACT

The present invention provides an insecticidal/acaricidal composition comprising, as active ingredients, (a) at least one pyrethroid compound selected from the group consisting of 3-phenoxybenzyl chrysanthemate and α-cyano-3-phenoxybenzyl chrysanthemate and (b) at least one N-aryldiazole compound selected from the group consisting of 4-(2-bromo-1,1,2,2-tetrafluoroethyl)-1-(3-chloro-5-trifluoromethylpyridine-2-yl)-2-methylimidazole, 5-amino-3-cyano-1-(2,6-dichloro-4-trifluoromethylphenyl-4-trifluorometylsulfinylpyrazole and 5-amino-3-cyano-1-(2,6-dichloro-4-trifluoromethylphenyl)-4-trifluoromethylsulfinylpyrazole and an insecticidal/acaricidal method which comprises applying the composition.

7 Claims, No Drawings

INSECTICIDAL/ACARICIDAL COMPOSITION

FIELD OF THE INVENTION

The present invention relates to an insecticidal/acaricidal composition which is particularly suitable for controlling cockroaches, and an insecticidal/acaricidal method.

BACKGROUND OF THE INVENTION

Heretofore, various insecticides and acaricides have been developed. However, they cannot sufficiently control cockroaches, which are typical sanitary insect pests.

OBJECTS OF THE INVENTION

Therefore, an object of the present invention is to provide an insecticidal/acaricidal composition, which is particularly suitable for controlling cockroaches.

Another object of the present invention is to provide an insecticidal/acaricidal method.

These objects as well as other objects and advantages of the present invention will become apparent to those skilled in the art from the following description.

SUMMARY OF THE INVENTION

According to the present invention, there is provided an insecticidal/acaricidal composition (hereinafter referred to as a "present composition") having good insecticidal/acaricidal activity, particularly good control effect against cockroaches through synergistic effect.

The present composition comprises, as active ingredients, (a) at least one pyrethroid compound selected from the group consisting of 3-phenoxybenzyl chrysanthemate and α-cyano-3-phenoxybenzyl chrysanthemate and (b) at least one N-aryldiazole compound selected from the group consisting of 4-(2-bromo- 1,1,2,2-tetrafluoroethyl)-1-(3-chloro-5-trifluoromethylpyridine- 2-yl)-2-methylimidazole represented by the formula:

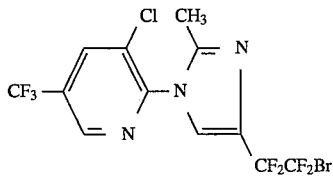

5-amino-3-cyano-1-(2,6-dichloro-4-trifluoromethylphenyl)-4-trifluoromethylsulfinylpyrazole represented by the formula:

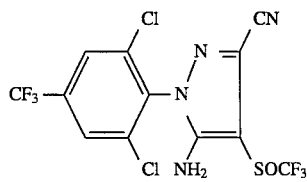

and 5-amino-3-cyano-1-(2,6-dichloro-4-trifluoromethylphenyl)- 4-trifluoromethylthiopyrazole represented by the formula:

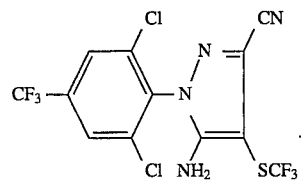

The present invention also provides a method for controlling noxious insect/acarine pests, which comprises applying, as active ingredients: (a) at least one pyrethroid compound selected from the group consisting of 3-phenoxybenzyl chrysanthemate and α-cyano-3-phenoxybenzyl chrysanthemate; and (b) at least one N-aryldiazole compound selected from the group consisting of 4-(2-bromo-1,1,2,2-tetrafluoroethyl)- 1-(3-chloro-5-trifluoromethylpyridine-2-yl)-2-methylimidazole, 5-amino-3-cyano-1-(2,6-dichloro-4-trifluoromethylphenyl)- 4-trifluoromethylsulfinylpyrazole and 5-amino-3-cyano-1-(2,6-dichloro-4-trifluoromethylphenyl)- 4-trifluoromethylthiopyrazole to the locus where noxious insect/acarine pests propagate in an amount by which synergistic insecticidal/acaricidal effect is shown.

DETAILED DESCRIPTION OF THE INVENTION

In the present invention, optically active compounds originated in asymmetric carbons exist in 3-phenoxybenzyl chrysanthemate and α-cyano-3-phenoxybenzyl chrysanthemate. In the present invention, any active isomers and a mixture thereof can be used, and examples thereof include 3-phenoxybenzyl (1R)-cis, trans-chrysanthemate, 3-phenoxybenzyl(1R)-trans-chrysanthemate, (RS)-α-cyano-3-phenoxybenzyl (1R)-cis, trans-chrysanthemate, (S)-α-cyano-3-phenoxybenzyl (1R)-cis, trans-chrysanthemate, (RS)-α-cyano-3-phenoxybenzyl (1R)-trans-chrysanthemate, (S)-α-cyano-3-phenoxybenzyl (1R)-trans-chrysanthemate and the like.

The N-aryldiazole compounds above are described in Japanese Patent Kokai (laid-open) Nos. 4- 211682 and 63-316771, and are produced according to a method described in the above gazettes.

In the present invention, the active ingredients are usually applied as a composition, and a mixing weight ratio of 3-phenoxybenzyl chrysanthemate or α-cyano-3-phenoxybenzyl chrysanthemate to the above N-aryldiazole compound is normally within a range from 9:1 to 5:95, preferably from 99:1 to 10:90, more preferably from 90:10 to 25:75.

The present composition has excellent insecticidal/acaricidal activity against various noxious insects or acarines. Particularly, it is useful for controlling cockroaches such as *Blattella germanica*, *Periplaneta fuliginosa*, *Periplaneta americana*, *Periplaneta brunnea*, *Blatta orientalis* and the like.

The active ingredient compounds in the present composition are normally mixed with solid carriers or liquid carrier or impregnated in a base material of mosquito-coil, mosquito-mat, etc. and, if necessary, surfactants and other auxiliary agents for formulation are added to formulate into forms such as oil solutions, emulsifiable concentrates, wettable powders, flowables (e.g. suspension in water, emulsion in water, etc.), granules, dusts, aerosols, heating fumigants (e.g. mosquito-coil, mosquito-mat for electric heating fumigation, a liquid formulation for electric heating fumigation, etc.), heating smoking formulations (e.g. self-combustion type smoking formulation, chemical reaction type smoking formulation, electric heating smoking formulation, etc.), fog formulations (e.g. fogging, etc.), ULV and the like.

These formulations normally contain the compound as an active ingredient in the total amount of 0.001 to 95% by weight.

Examples of the solid carrier to be used for the formulation include fine powders or granules of clays (e.g. kaolin clay, diatomaceous earth, bentonite, Fubasami clay, acid clay, etc.), synthetic hydrated silicon oxide, talcs, ceramics, other inorganic minerals (e.g. sericite, quartz, sulfur, active carbon, calcium carbonate, hydrated silica, etc.), commercial fertilizers (e.g. ammonium sulfate, ammonium phosphate, ammonium nitrate, urea, ammonium chloride, etc.) and the like.

Examples of the liquid carrier include water, alcohols (e.g. methanol, ethanol, etc.), ketones (e.g. acetone, methyl ethyl ketone, cyclohexanone, etc.), aromatic hydrocarbons (e.g. benzene, toluene, xylene, ethylbenzene, methylnaphthalene, etc.), non-aromatic hydrocarbons (e.g. hexane, cyclohexane, kerosine, gas oil, etc.), esters (e.g. ethyl acetate, butyl acetate, etc.), nitriles (e.g. acetonitrile, isobutylnitrile, etc.), ethers (e.g. diisopropyl ether, dioxane, etc.), acid amides (e.g. N,N-dimethylformamide, N,N-dimethylacetamide, etc.), halogenated hydrocarbons (e.g. dichloromethane, trichloroethane, carbon tetrachloride, etc.), dimethyl sulfoxide, vegetable oils (e.g. soybean oil, cottonseed oil, etc.) and the like.

If necessary, propellants such as flon gas, butane gas, liquefied petroleum gas, dimethyl ether, carbon dioxide gas, etc. can be used for the formulation.

Examples of the surfactant include alkyl sulfates, salts of alkyl sulfonate, alkyl aryl sulfonates, alkyl aryl ethers, polyoxyethylene compounds thereof, polyethylene glycol ethers, polyhydric alcohol esters, sugar alcohol derivatives and the like.

Examples of the other auxiliary agent for formulation such as fixing agent and dispersing agent include casein, gelatin, saccharides (e.g. starch powder, gum arabic, cellulose derivative, alginic acid, etc.), lignin derivatives, bentonite, synthetic water-soluble polymers (e.g. polyvinyl alcohol, polyvinyl pyrrolidone, polyacrylic acids, etc.) and the like. Further, there can also be used stabilizers such as PAP (isopropyl acid phosphate), BHT (2,6-di-tert-butyl-4-methylphenol), BHA (2-tert-butyl-4-methoxyphenol and 3-tert-butyl- 4-methoxyphenol), vegetable oils, mineral oils, fatty acids or esters thereof, etc. as the auxiliary agent for formulation.

Examples of the base material of mosquito-coils include mixtures of vegetable flours (e.g. wood flour, rice bran flour, etc.) and binders (e.g. flour of *Machilus thunbergii* Sieb et Zucc., starch powder, gluten, etc.).

Examples of the base material of mosquito-mats include those prepared by molding a fibril of cotton linter or a mixture of cotton linter and pulp into a plate.

Examples of the base material of the self-combustion type smoking formulation include combustion exothermic agents (e.g. nitrate, nitrite, guanidine salt, potassium chlorate, nitrocellulose, ethyl-cellulose, wood flour, etc.), pyrolysis stimulants (e.g. alkali metal salt, bichromate, chromate, etc.), oxygen suppliers (e.g. potassium nitrate, etc.), combustion asistant (e.g. melamine, wheat starch, etc.), bulking agents (e.g. diatomaceous earth, etc.), binders (e.g. synthetic starch, etc.) and the like.

Examples of the base material of the chemical reaction type smoking formulation include exothermic agents (e.g. sulfide, polysulfide, water sulfide and hydrated salt of alkali metal, calcium oxide, etc.), catalysts (e.g. carbonaceous substance, iron carbide, activated clay, etc.), organic foaming agents (e.g. azodicarbonimide, benzenesulfonyl hydrazide, dinitrosopentamethylenetetramine, polystyrene, polyurethane, etc.), fillers (e.g. natural fiber fragment, etc.) and the like.

Flowables (e.g. suspension in water, emulsion in water, etc.) can be obtained by finely dispersing 1 to 75% by weight of the compound as active ingredient in water containing 0.5 to 15% by weight of a suspension auxiliary (e.g. protective colloid, compound imparting thixotropic properties, etc.) and 0 to 10% by weight of an auxiliary agent (e.g. defoamer, rust preventive, stabilizer, spreading agent, penetration auxiliary, antifreezing agent, antibacterial agent, antifungal substance, etc.). In place of the water, an oil in which the active ingredient compounds are hardly dissolved can be used to obtain a suspension in oil.

As the protective colloid, for example, there can be used gelatin, casein, gums, cellulose ether, polyvinyl alcohol and the like. Examples of the compound imparting thixotropic properties include bentonite, aluminum magnesium silicate, xanthangum, polyacrylic acid and the like.

The formulations thus obtained can be used as prepared or after diluted, for example, with water. On the practical use of the formulations containing the compounds as active ingredients, emulsifiable concentrates, wettable powders and flowables are normally diluted with water to the concentration of about 1 to 10000 ppm. Oil solutions, aerosols, fumigants, smoking formulations, fog formulations, ULV, etc. are used as prepared. Further, they can also be used simultaneously with other insecticides, acaricides, fungicides and the like.

The application rate of these formulations varies depending on the kind of noxious insect to be controlled, type of formulation, place and method of application and the like. The application rate of the present composition is normally about 0.0001 to 10 $g/m^2$ based on the weight of the active ingredients.

For controlling cockroaches, it is effective to spray an aerosol containing the present composition in an amount of about 0.001 to 1 g per 1 $m^2$ based on the active ingredients, or a heating fumigant or heating smoke formulation is used to vaporize the active ingredients in an amount of about 0.0001 to 1 g per 1 $m^3$.

In the insecticidal/acaricidal method of the present invention, it is advantageous to use the present composition wherein 3-phenoxybenzyl chrysanthemate or α-cyano-3-phenoxybenzyl chrysanthemate are mixed in advance with the above aryldiazole compound. Moreover, the active ingredients do not have to be mixed for application and each of the active ingredients or formulations thereof can be applied at the same time or successively in appropriate methods for each of the ingredients or formulations thereof. For example, the pyrethroid compound and the aryldiazole compound can be applied as active ingredients independently but at the same time or successively in an amount by which a synergistic insecticidal/acaricidal effect is shown.

The following Formulation Examples and Test Examples further illustrate the the present invention in detail, but are not to be construed to limit the scope thereof.

Formulation Example 1

0.5 Part by weight of 3-phenoxybenzyl (1R)-cis, trans-chrysanthemate, 0.1 part by weight of 5-amino- 3-cyano-1-

(2,6-dichloro-4-trifluoromethylphenyl)- 4-trifluoromethylsulfinylpyrazole, 49.7 parts by weight of Isopar M (aliphatic hydrocarbon, manufactured by Exxon Chemical Co.) and 49.7 parts by weight of Chlorosen Nu (chlorinated hydrocarbon, manufactured by Dow Chemical Co.) are mixed to give an oil solution of the present invention.

Formulation Example 2

1 Part by weight of 3-phenoxybenzyl (1R)-cis, trans-chrysanthemate, 0.1 part by weight of 5-amino-3-cyano-1-(2,6-dichloro-4-trifluoromethylphenyl)-4-trifluoromethylsulfinylpyrazole, 49.45 parts by weight of Isopar M and 49.45 parts by weight of Chlorosen Nu are mixed to give an oil solution of the present invention.

Formulation Example 3

0.5 Part by weight of α-cyano-3-phenoxybenzyl (1R)-cis, trans-chrysanthemate, 0.1 part by weight of 5-amino- 3-cyano-1-(2,6-dichloro-4-trifluoromethylphenyl)- 4-trifluoromethylsulfinylpyrazole and 99.4 parts by weight of kerosene are mixed to give an oil solution of the present invention.

Formulation Example 4

1 Part by weight of 3-phenoxybenzyl (1R)-cis, trans-chrysanthemate, 0.1 part by weight of 5-amino-3-cyano-1-(2,6-dichloro-4-trifluoromethylphenyl)-4-trifluoromethylsulfinylpyrazole and 98.9 parts by weight of a diesel oil are mixed to give an oil solution of the present invention.

Test Example 1

A triangle shelter (having a shape of triangular prism which was made by combining three plywood plates of 15 cm in length and 3.5 cm in width) in which 5 female adult Blattella germanica were charged was placed on two corners which correspond to both ends of a diagonal line in a floor of a room (28 $m^3$), respectively. On the other hand, a ceramic plate (4 cm× 4 cm×1.2 cm) impregnated with an acetone solution of a test chemical was placed on the center of the floor of the room. Then, (S)-α-cyano-3-phenoxybenzyl (1R)-cis, trans-chrysanthemate [described as a "compound (I)"] and 5-amino-3-cyano-1-(2,6-dichloro-4-trifluoromethylphenyl)- 4-trifluoromethylsulfinylpyrazole [described as a "compound (II)"] were vaporized by heating at 250° C. and 200° C. for 60 minutes, respectively, using an electric heater. 120 Minutes after the beginning of heating, test insects were transferred to the other container and examined to determine the mortality after 3 days. The results are shown in Table 1.

TABLE 1

| Test compound | Amount of chemical (mg/$m^3$) | Mortality (%) |
| --- | --- | --- |
| Compound (I) | 2.35 | 0 |
| Compound (II) | 0.78 | 0 |
| Compound (I) + Compound (II) | 2.35 + 0.78 | 100 |

Test Example 2

A triangle shelter (having a shape of triangular prism which was made by combining three plywood plates of 15 cm in length and 3.5 cm in width) in which 3 female adult Periplaneta americana were charged was placed on two corners which correspond to both ends of a diagonal line in a floor of a room (28 $m^3$), respectively. On the other hand, a ceramic plate (4 cm×4 cm×1.2 cm) impregnated with an acetone solution of a test chemical was placed on the center of the floor of the room. Then, the compounds (I) and (II) were transpirated by heating at 250° C. and 200° C. for 60 minutes, respectively, using an electric heater. 120 Minutes after the beginning of heating, test insects were transferred to the other container and examined to determine the mortality after 3 days. The results are shown in Table 2.

TABLE 2

| Test compound | Amount of chemical (mg/$m^3$) | Mortality (%) |
| --- | --- | --- |
| Compound (I) | 1.56 | 0 |
| Compound (II) | 50 | 0 |
| Compound (I) + Compound (II) | 1.56 + 50 | 100 |

Test Example 3

A triangle shelter (having a shape of triangular prism made by combining three plywood plates of 15 cm in length and 3.5 cm in width) in which 5 female adult Blattella germanica were charged was allowed to stand on a floor of a glass chamber (0.34 $m^3$). Then, 4 ml (0.8 atm) of an oil solution containing 3-phenoxybenzyl (1R)-cis, trans-chrysanthemate [described as a "compound (III)"] and the above compound (II) in a predetermined concentration, which was formulated according to the same manner as that described in Formulation Example 1, was sprayed into the glass chamber. 10 Minutes after spraying, the glass chamber was ventilated for 3 minutes. Thereafter, test insects were transferred to the other container and examined to determine the mortality after 1 days. The results are shown in Table 3.

TABLE 3

| Test compound | Concentration (%) | Mortality (%) |
| --- | --- | --- |
| Compound (III) | 0.5 | 0 |
| Compound (II) | 0.1 | 20 |
| Compound (III) + Compound (II) | 0.5 + 0.1 | 100 |

Test Example 4

A triangle shelter (having a shape of triangular prism made by combining three plywood plates of 15 cm in length and 3.5 cm in width) in which 3 female adult Periplaneta americana were charged was allowed to stand on a floor of a glass chamber (0.34 $m^3$). Then, 4 ml (0.8 atm) of an oil solution containing 3-phenoxybenzyl (1R)-cis, trans-chrysanthemate [described as a "compound (III)"] and the above compound (II) in a predetermined concentration, which was formulated according to the same manner as that described in Formulation Example 2, was sprayed into the glass chamber. 15 Minutes after spraying, the glass chamber was ventilated for 5 minutes. Thereafter, test insects were transferred to the other container and examined to determine the mortality after 3 days. The results are shown in Table 4.

TABLE 4

| Test compound | Concentration (%) | Mortality (%) |
| --- | --- | --- |
| Compound (III) | 1 | 33 |
| Compound (II) | 0.1 | 0 |
| Compound (III) + Compound (II) | 1 + 0.1 | 100 |

What is claimed is:

1. An insecticidal and acaricidal composition comprising, as active ingredients, synergistic effective amounts of: (a) a pyrethroid compound which is (S)-α-cyano-3-phenoxybenzyl (1R)-cis, trans-chrysanthemate and (b) an N-aryldiazole compound which is 5-amino-3-cyano-1-(2,6-dichloro- 4-trifluoromethylphenyl)-4-trifluoromethylsulfinylpyrazole, wherein the weight ratio of the pyrethroid compound (a) to the N-aryldiazole compound (b) is within a range of from 99:1 to 5:95.

2. The insecticidal and acaricidal composition according to claim 1, wherein the weight ratio of the pyrethroid compound (a) to the N-aryldiazole compound (b) is within a range of from 99:1 to 10:90.

3. The insecticidal and acaricidal composition according to claim 1, wherein the weight ratio of the pyrethroid compound (a) to the N-aryldiazole compound (b) is within a range of from 90:10 to 25:75.

4. A method for controlling noxious insect and acarine pests, which comprises applying to a locus where noxious insect and acarine pests propogate an effective amount of the composition comprising, as active ingredients, synergistic effect amounts of: (a) a pyrethroid compound which is (S)-α-cyano-3-phenoxybenzyl (1R)-cis, trans-chrysanthemate and (b) an N-aryldiazole compound which is 5-amino-3-cyano-1-(2,6-dichloro-4-trifluoromethylphenyl) -4-trifluoromethylsulfinylpyrazole, wherein the weight ratio of the pyrethroid compound (a) to the N-aryldiazole compound (b) is within a range of from 99:1 to 5:95.

5. The method according to claim 4, wherein the insect pests are cockroaches.

6. The method according to claim 4, wherein the weight ratio of the pyrethroid compound (a) to the N-aryldiazole compound (b) is within a range of from 99:1 to 10:90.

7. The method according to claim 4, wherein the weight ratio of the pyrethroid compound (a) to the N-aryldiazole compound (b) is within a range of from 90:10 to 25:75.

* * * * *